(12) United States Patent
Kuramori et al.

(10) Patent No.: US 8,296,013 B2
(45) Date of Patent: Oct. 23, 2012

(54) METHOD AND SYSTEM FOR EVALUATING DRIVING CONDITIONS OF A VEHICLE

(75) Inventors: Akira Kuramori, Kanagawa (JP); Masayoshi Kamijo, Nagano (JP)

(73) Assignee: The Yokohama Rubber Co., Ltd., Tokyo (JP)

( * ) Notice: Subject to any disclaimer, the term of this patent is extended or adjusted under 35 U.S.C. 154(b) by 708 days.

(21) Appl. No.: 12/433,990

(22) Filed: May 1, 2009

(65) Prior Publication Data

US 2009/0287374 A1 Nov. 19, 2009

(30) Foreign Application Priority Data

May 14, 2008 (JP) .................................. 2008-127213

(51) Int. Cl.
*A01B 69/00* (2006.01)
*B62D 6/00* (2006.01)
*B62D 11/00* (2006.01)
*B62D 12/00* (2006.01)
*B63G 8/20* (2006.01)
*B63H 25/04* (2006.01)
*G05D 1/00* (2006.01)
*G06F 7/00* (2006.01)
*G06F 17/00* (2006.01)
*G06F 19/00* (2006.01)

(52) U.S. Cl. ........................................................ 701/41

(58) Field of Classification Search ....................... 701/41
See application file for complete search history.

(56) References Cited

U.S. PATENT DOCUMENTS

| 6,079,258 A | 6/2000 | List et al. |
| 6,499,559 B2 * | 12/2002 | McCann et al. ............... 180/446 |
| 2005/0080350 A1 * | 4/2005 | Kuramori et al. ............. 600/546 |

FOREIGN PATENT DOCUMENTS

| EP | 0 846 945 | 6/1998 |
| EP | 1 516 587 | 3/2005 |
| EP | 1 882 619 | 1/2008 |

(Continued)

OTHER PUBLICATIONS

Kuramori et al.; "Study on Driving Ease Evaluation Focusing on Muscular Activity of Driver;" Jidosha Gijutsu, Jidosha Gijutsukai, JP, vol. 61, No. 6; Jun. 1, 2007; pp. 116-121.

(Continued)

*Primary Examiner* — Khoi Tran
*Assistant Examiner* — Nicholas Kiswanto
(74) *Attorney, Agent, or Firm* — Greer, Burns & Crain, Ltd

(57) ABSTRACT

The method and system evaluate driving conditions of a vehicle whereby drivability of the vehicle can be evaluated accurately and objectively. To evaluate drivability of the vehicle under different driving conditions, a plural pieces of driving load information including biological information on a driver and movement information of the vehicle being driven are measured. Then, a group of weighting coefficients as many as or fewer than pieces of the driving load information is selected from groups of weighting coefficients that are set according to representative values of the driving load information in order to use a weighted linear sum of the representative values of the driving load information as an index of an integrated evaluation of the drivability of the vehicle. Subsequently, a weighted linear sum is obtained using the selected group of weighting coefficients and used to perform the integrated evaluation of the drivability under various driving conditions.

11 Claims, 9 Drawing Sheets

FOREIGN PATENT DOCUMENTS

| | | |
|---|---|---|
| EP | 2 063 247 | 5/2009 |
| JP | A 2005-87485 | 4/2005 |
| JP | 2006-254107 | 9/2006 |
| JP | A 2007-280 | 1/2007 |
| WO | WO 2006/131256 A1 | 12/2006 |
| WO | WO 2008/032656 | 3/2008 |

OTHER PUBLICATIONS

Kuramori et al.; "Evaluation of Vehicle Drivability using Electromyogram Analysis;" Proceedings—JSAE Annual Congress—Gakujutsu Koenkai Maezurishu, Jidosha Gijutsukai, Japan; vol. 92-00, pp. 9-14; Jan. 1, 2000.

* cited by examiner

FIG.5

| | | VEHICLE MOVEMENT INFORMATION | | | | BIOLOGICAL INFORMATION | | | | |
|---|---|---|---|---|---|---|---|---|---|---|
| | | RMS(*) | | RMS(*) OF AMOUNT OF CHANGE OF WAVEFORM | | RMS(*) | | | RMS(*) OF AMOUNT OF CHANGE OF WAVEFORM | |
| DRIVERS | TIRES | STEERING ANGLE | STEERING TORQUE | STEERING ANGLE | STEERING TORQUE | LEFT DELTOID MUSCLE | RIGHT DELTOID MUSCLE | SIMULTANEOUS R/L DELTOID MUSCLE CONTRACTION () | LEFT DELTOID MUSCLE | RIGHT DELTOID MUSCLE | SIMULTANEOUS R/L DELTOID MUSCLE CONTRACTION () |
| P1 | A | 1.024 | 1.024 | 1.163 | 1.051 | 1.262 | 1.009 | 1.162 | 1.192 | 1.044 | 1.125 |
| P2 | A | 1.019 | 1.020 | 1.086 | 1.029 | 0.909 | 1.051 | 1.006 | 1.046 | 1.057 | 1.031 |
| P3 | A | 1.030 | 1.029 | 1.109 | 1.082 | 1.045 | 1.010 | 1.028 | 1.027 | 1.017 | 0.999 |
| P4 | A | 1.027 | 1.035 | 1.046 | 1.059 | 1.327 | 1.033 | 1.168 | 1.310 | 1.081 | 1.201 |
| P5 | A | 1.027 | 1.039 | 1.244 | 1.095 | 1.139 | 0.986 | 1.011 | 1.336 | 1.071 | 1.132 |
| P6 | A | 1.042 | 1.044 | 1.065 | 1.047 | 0.901 | 1.060 | 0.971 | 0.957 | 1.091 | 1.002 |
| P7 | A | 1.035 | 1.037 | 1.034 | 1.054 | 0.999 | 1.147 | 1.086 | 0.974 | 1.043 | 0.965 |
| P8 | A | 1.040 | 1.051 | 1.108 | 1.054 | 1.106 | 0.987 | 1.048 | 1.102 | 1.006 | 1.072 |
| P1 | B | 0.955 | 0.946 | 1.021 | 0.957 | 1.075 | 0.948 | 1.018 | 1.169 | 1.017 | 1.075 |
| P2 | B | 0.963 | 0.960 | 0.895 | 0.968 | 0.822 | 0.987 | 0.944 | 0.769 | 0.981 | 0.935 |
| P3 | B | 0.960 | 0.951 | 1.012 | 0.925 | 1.005 | 1.001 | 1.004 | 1.021 | 0.956 | 0.972 |
| P4 | B | 0.957 | 0.941 | 1.060 | 0.934 | 0.945 | 1.018 | 0.968 | 1.123 | 1.031 | 1.109 |
| P5 | B | 0.960 | 0.939 | 0.841 | 0.932 | 1.048 | 0.902 | 0.952 | 1.013 | 0.936 | 0.998 |
| P6 | B | 0.955 | 0.938 | 0.874 | 0.929 | 0.937 | 0.944 | 0.933 | 0.994 | 0.933 | 0.946 |
| P7 | B | 0.960 | 0.946 | 0.942 | 0.950 | 1.184 | 0.923 | 1.008 | 1.476 | 0.983 | 1.043 |
| P8 | B | 0.949 | 0.939 | 1.017 | 0.946 | 0.967 | 0.997 | 0.984 | 0.985 | 0.992 | 0.984 |
| P1 | C | 1.021 | 1.031 | 0.815 | 0.992 | 0.863 | 1.045 | 0.820 | 0.640 | 0.939 | 0.800 |
| P2 | C | 1.019 | 1.019 | 1.019 | 1.003 | 1.269 | 0.982 | 1.050 | 1.185 | 0.962 | 1.034 |
| P3 | C | 1.010 | 1.020 | 0.878 | 0.993 | 0.950 | 0.989 | 0.968 | 0.952 | 1.027 | 1.029 |
| P4 | C | 1.017 | 1.025 | 0.894 | 1.007 | 0.727 | 0.949 | 0.864 | 0.567 | 0.888 | 0.690 |
| P5 | C | 1.013 | 1.022 | 0.915 | 0.973 | 0.812 | 1.112 | 1.036 | 0.651 | 0.994 | 0.870 |
| P6 | C | 1.003 | 1.018 | 1.081 | 1.024 | 1.162 | 0.996 | 1.098 | 1.048 | 0.976 | 1.052 |
| P7 | C | 1.005 | 1.016 | 1.024 | 0.996 | 0.818 | 0.930 | 0.905 | 0.550 | 0.974 | 0.992 |
| P8 | C | 1.011 | 1.010 | 0.875 | 1.001 | 0.927 | 1.016 | 0.969 | 0.913 | 1.002 | 0.944 |

*: ROOT MEAN SQUARE
**: SIMULTANEOUS RIGHT AND LEFT DELTOID MUSCLE CONTRACTION

FIG.6A

| | EIGENVALUE | CONTRIBUTION RATIO | CUMULATIVE CONTRIBUTION RATIO |
|---|---|---|---|
| PRINCIPAL COMPONENT 1 | 4.92 | 0.49 | 0.49 |
| PRINCIPAL COMPONENT 2 | 2.96 | 0.30 | 0.79 |
| PRINCIPAL COMPONENT 3 | 0.86 | 0.09 | 0.87 |

FIG.6B

| PRINCIPAL COMPONENT LOADING | PRINCIPAL COMPONENT 1 | PRINCIPAL COMPONENT LOADING | PRINCIPAL COMPONENT 2 | PRINCIPAL COMPONENT LOADING | PRINCIPAL COMPONENT 3 |
|---|---|---|---|---|---|
| RMS.DltLR | 0.83 | RMS.TRQ | 0.79 | RMS.DltR | 0.67 |
| dRMS.STA | 0.82 | RMS.STA | 0.77 | dRMS.DltR | 0.39 |
| dRMS.DltR | 0.82 | RMS.DltR | 0.58 | RMS.DltLR | 0.13 |
| dRMS.TRQ | 0.77 | dRMS.TRQ | 0.53 | dRMS.DltLR | 0.05 |
| dRMS.DltLR | 0.76 | dRMS.DltR | 0.04 | dRMS.DltL | -0.04 |
| RMS.DltL | 0.73 | dRMS.STA | -0.07 | dRMS.STA | -0.06 |
| dRMS.DltL | 0.64 | RMS.DltLR | -0.26 | RMS.STA | -0.22 |
| RMS.STA | 0.57 | dRMS.DltLR | -0.55 | RMS.DltL | -0.23 |
| RMS.TRQ | 0.54 | RMS.DltL | -0.56 | RMS.TRQ | -0.24 |
| RMS.DltR | 0.38 | dRMS.DltL | -0.67 | dRMS.TRQ | -0.28 |

RMS.☐ = RMS OF ☐
dRMS.☐ = RMS OF AMOUNT OF CHANGE OF ☐

DltLR = WAVEFORM OF SIMULTANEOUS DELTOID MUSCLE CONTRACTION
DltR = RIGHT DELTOID MUSCLE
DltL = LEFT DELTOID MUSCLE
STA = STEERING ANGLE
TRQ = STEERING TORQUE

METHOD AND SYSTEM FOR EVALUATING DRIVING CONDITIONS OF A VEHICLE

BACKGROUND OF THE INVENTION

The present invention relates to a method and a system for evaluating driving conditions of a vehicle whereby drivability is evaluated as the vehicle is driven under different driving conditions.

In recent years, various proposals have been made to provide ways of detecting biological information on a driver driving a vehicle and using such information for vehicle control. Further, various proposals have also been made to provide methods for evaluating drivability of a vehicle by using a driver's myoelectric potentials.

For example, JP 2005-087485 A describes a method whereby a driver's myoelectric potentials such as those of his/her deltoid muscles are measured as the driver steers a vehicle in order to evaluate the drivability thereof.

JP 2005-087485 A proposes a device for evaluating the degree of operation comfort felt during operation. The device therein described uses a detection sensor to detect myoelectric potentials of a plurality of muscles generated by the muscle activities of the human body as the driver steers a vehicle or otherwise operates the vehicle. The detected myoelectric potentials are amplified to produce myoelectric potential waveforms, which are used to generate a simultaneous contraction intensity of those muscles. On the other hand, the level of operation load intensity generated during operations is calculated at the timing of the generation of a simultaneous contraction intensity to normalize the simultaneous contraction intensity with the calculated operation load intensity level in order to evaluate the degree of operation comfort. This enables evaluation of the degree of operation comfort according to the description.

JP 2007-000280 A, on the other hand, describes a device that measures signals from such biomarkers as brain waves, respiration, body temperature, nictitation, and cardiac beats and uses these biomarkers to determine the driver's wakefulness level in order to accurately determine his/her decreased wakefulness as he/she drives.

SUMMARY OF THE INVENTION

According to the device described in JP 2005-087485 A, the degree of operation comfort is evaluated by normalizing a simultaneous muscle contraction intensity that is obtained from biological information of a test subject and which changes greatly according to the mental stresses felt by the test subject. The simultaneous contraction waveform thereof alone, however, cannot necessarily guarantee sufficient evaluation of the operation comfort and ease of operation.

On the other hand, the device described in JP 2007-000280 A is proposed for determining the decreased level of a driver's wakefulness and not for evaluating the drivability of a vehicle felt by the driver.

It is an object of the present invention to provide a method and a system for evaluating driving conditions of a vehicle whereby drivability of the vehicle can be evaluated accurately and objectively.

To achieve the above object, the present invention provides a method of evaluating driving conditions of a vehicle whereby drivability of the vehicle driven by a driver under different driving conditions is evaluated, the method comprising a step of measuring biological information on a driving driver and movement information of the vehicle being driven as driving load information, and acquiring a group of representative values, which is obtained from a measurement result of such information, for each driving condition, a step of selecting a group of weighting coefficients in a number equal to or less than a number of pieces of the driving load information from groups of weighting coefficients that are set according to representative values of the driving load information for each driving condition, and a step of obtaining a weighted linear sum using a selected group of the weighting coefficients and using the weighted linear sum to perform an integrated evaluation of the drivability under each driving condition.

Preferably, the different driving conditions comprise driving conditions in which the vehicle and a track used for driving are identical and tires attached to the vehicle are varied.

Preferably, the biological information is information on muscle activities measured as the driver makes voluntary movements to drive the vehicle.

Preferably, the biological information contains at least one of a stationary component of a muscle activity in a given time and a nonstationary component of a muscle activity in a given time out of information on muscle activities measured as the driver makes the voluntary movements.

Preferably, the biological information is at least one information selected from myoelectric potentials, brain waves, respiration rate, body temperature, nictitation frequency, cardiac rate, pulse rate, blood flow rate, amount of perspiration, and electrodermal activity.

Preferably, the movement information of the vehicle contains at least one of a steering angle imparted by the driver to a steering wheel, a steering angular velocity imparted by the driver to the steering wheel, a steering torque imparted by the driver to the steering wheel, steering power imparted by the driver to the steering wheel, a forward/backward acceleration at a vehicle barycenter, a forward/backward jerk at the vehicle barycenter, lateral acceleration at the vehicle barycenter, a lateral jerk at the vehicle barycenter, a vertical acceleration at the vehicle barycenter, a vertical jerk at the vehicle barycenter, a yaw angular velocity about the vehicle barycenter, a yaw angular acceleration about the vehicle barycenter, a roll angle about the vehicle barycenter, a roll angular velocity about the vehicle barycenter, a side slip angle at the vehicle barycenter, and a side slip angular velocity at the vehicle barycenter.

Preferably, the driving load information is measured for a plurality of drivers, and the representative values of the driving load information are values obtained by normalizing data of the driving load information for each of the drivers.

Preferably, each of the weighting coefficients is a value of each component of eigenvectors obtained by performing major component analysis on the representative values of the driving load information.

It is preferable that in the step of selecting the group of weighting coefficients, when a cumulative contribution ratio is determined by adding contribution ratios of eigenvalues obtained by the principal component analysis to the sum of all the eigenvalues in descending order, eigenvalues contributing to the cumulative contribution ratio are taken out on the condition that the cumulative contribution ratio is less than 0.8, and values of components of eigenvectors corresponding to the eigenvalues are used as values of the weighting coefficients.

It is preferable that in the step of selecting the group of weighting coefficients, the group of weighting coefficients is selected by referring to a result of a sensory evaluation by the driver.

The present invention further provides a system of evaluating driving conditions of a vehicle whereby drivability of the vehicle driven by a driver under different driving conditions is evaluated, the system comprising a unit for measuring a plurality of pieces of driving load information containing biological information on a driving driver and movement information of the vehicle being driven, and acquiring representative values of driving load information obtained from a measurement result of such information, a unit for selecting a group of weighting coefficients in a number equal to or less than a number of pieces of the driving load information from groups of weighting coefficients that are set according to representative values of the driving load information in order to use a weighted linear sum of the representative values of the driving load information as an index of an integrated evaluation of the drivability of the vehicle, and a unit for obtaining the weighted linear sum using a selected group of the weighting coefficients and using the weighted linear sum to perform the integrated evaluation of the drivability under each driving condition.

In the present invention, biological information on a driver driving a vehicle and movement information on the vehicle being driven are used as driving load information to provide a weighted linear sum of representative values of a plurality of pieces of driving load information as an index for an overall or integrated evaluation as to the drivability of the vehicle. A weighted linear sum is obtained by selecting one from among a plurality of groups of weighting coefficients that are set according to representative values of driving load information acquired by measurement. Thus, use of the weighted linear sum allows an accurate overall evaluation of drivability under various driving conditions in a way that reflects the driver's sensations.

Further, the integrated evaluation of drivability achieved using the weighted linear sum reduces to a minimum the effects of variations attributable to the driver's sensory evaluation and thus enables an objective overall evaluation excluding the driver's subjectivity.

In particular, selection of a group of weighting coefficients by referring to the driver's sensory evaluation result enables an integrated evaluation using values corresponding to the driver's sensory evaluation result.

BRIEF DESCRIPTION OF THE DRAWINGS

This and other objects, features, and advantages of the present invention will be apparent from the following detailed description and accompanying drawings in which:

FIG. 5 is a table showing examples of representative values of driving load information used in the method for evaluating driving conditions of a vehicle according to the invention.

FIGS. 6A and 6B are tables showing examples of principal component analysis results obtained in the method for evaluating driving conditions of a vehicle according to the invention.

DETAILED DESCRIPTION OF THE INVENTION

Now the method and the system for evaluating driving conditions of a vehicle according to the invention will be described in detail below by referring to preferred embodiments illustrated in the accompanying drawings.

Figure 1:
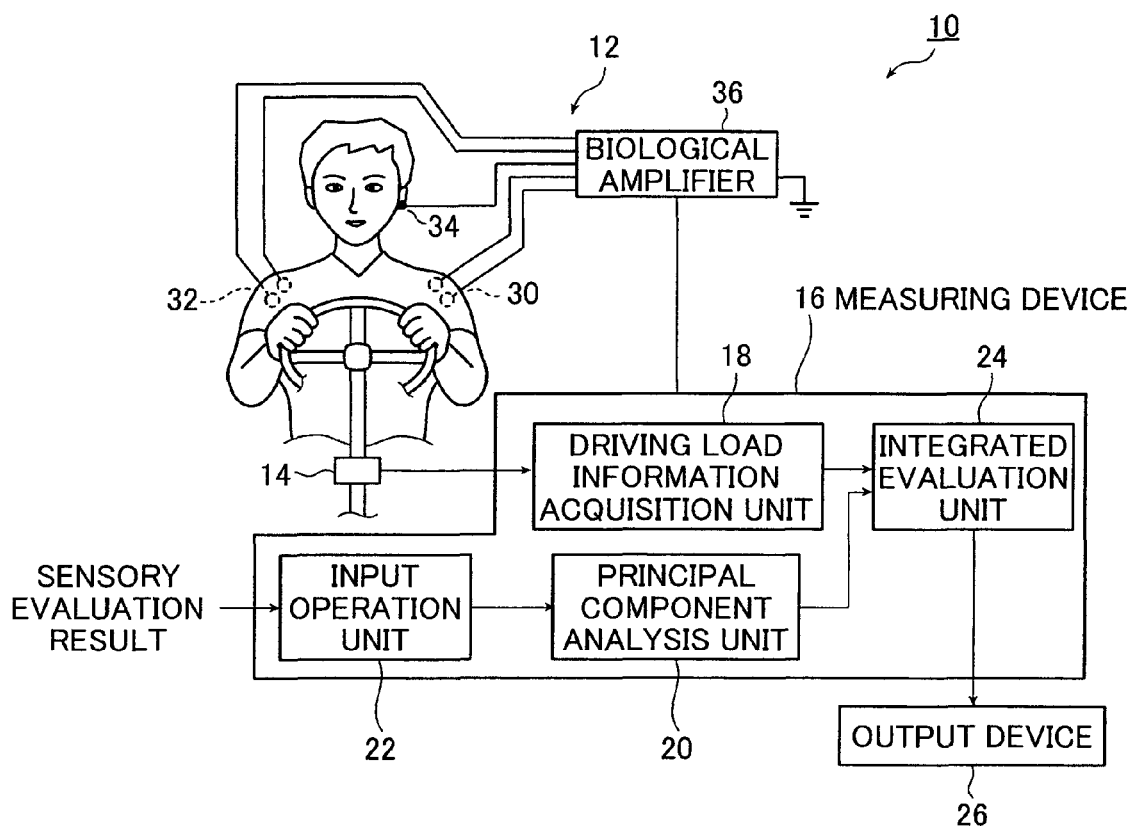
FIG. 1 is a view illustrating a configuration of an embodiment of the system for evaluating driving conditions of a vehicle according to the invention.

FIG. 1 illustrates a configuration of an embodiment of the system for evaluating driving conditions of a vehicle according to the invention.

An evaluation system 10 illustrated in FIG. 1 measures a plurality of pieces of driving load information as a driver drives a vehicle under a plurality of driving conditions to find representative values of the driving load information obtained from the measurement results. Using the representative values, the evaluation system 10 performs principal component analysis to extract some principal components. Then, using a weighted linear sum of the representative values for the principal components, the evaluation system 10 performs an overall or integrated evaluation of drivability under each driving condition. The embodiment described below uses information on the myoelectric potentials of a driver's right and left deltoid muscles as biological information in the driving load information on the one hand and information on a vehicle's steering angle and steering torque as the vehicle's movement information in the driving load information on the other.

The evaluation system 10 comprises a measuring device 12 for measuring information on myoelectric potentials, a steering angle/steering torque meter 14, and an evaluation device 16.

As illustrated in FIG. 1, the evaluation device 16 comprises a driving load information acquisition unit 18, a principal component analysis unit 20, an entry operation unit 22, and an integrated evaluation unit 24, and is connected with an output device 26. The evaluation device 16 does not perform online processing while the vehicle is actually being driven by the driver but performs offline processing by recording measurement data obtained by the measuring device 12 and the steering angle/steering torque meter 14 in a recording medium and then reproducing the recorded data.

The measuring device 12 comprises myoelectric sensors 30, 32, a ground electrode 34, and a biological amplifier 36.

The myoelectric sensor 30 comprises a pair of Ag/AgCL dish-shaped electrodes, which are attached to skin surface with a given distance, say several millimeters, from each other. In this embodiment, the myoelectric sensor 30 is a pair of dish-shaped electrodes attached, with a distance of about 5 mm from each other, to skin surface of the left shoulder where the left deltoid muscle is located to detect myoelectric potentials of the deltoid muscle of the driver's left shoulder. The Ag/AgCl electrodes are formed by coating the surface of a metallic silver material with an AgCl film and possess effective electric properties among re-usable general-purpose electrodes. The electrodes of the myoelectric sensors 30, 32 need not necessarily be Ag/AgCl electrodes and may be formed of stainless steel, carbon, carbon composites, platinum, gold, silver, titanium, a conductive resin, a conductive polymer gel and other materials as appropriate.

The myoelectric sensor 32 is a pair of dish-shaped electrodes as is the myoelectric sensor 30, and attached with a distance of about 5 mm from each other to skin surface of the right shoulder where the right deltoid muscle is located to detect a myoelectric potential of the deltoid muscle of the driver's right shoulder.

The myoelectric potential signals obtained by the myoelectric sensors 30, 32 are feeble and, therefore, a ground electrode 34 is used to remove ambient noise. The ground electrode 34 is connected to the biological amplifier 36 and grounded through the biological amplifier 36.

The biological amplifier 36 is connected with the myoelectric sensors 30, 32 through lead wires. Since most myoelectric potentials detected by the myoelectric sensors 30, 32 are as feeble as on the order of several microvolts to several millivolts and, therefore, their voltages are amplified by the biological amplifier 36 to a level permitting an analog-to-digital conversion. The myoelectric potential signals amplified by the biological amplifier 36 are subjected to an analog-to-digital conversion at a given sampling frequency to produce digital signals, which are transmitted to the evaluation device 16.

Figure 2:
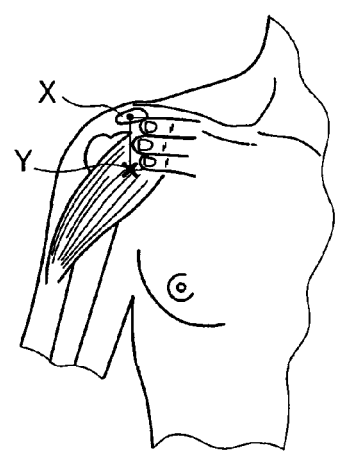
FIG. 2 is a view for explaining a method of measuring biological information used in the method for evaluating driving conditions of a vehicle according to the invention.

FIG. 2 illustrates how the myoelectric sensors 30, 32 are attached. A deltoid muscle is a triangular muscle covering a large area of the shoulder and used to rotate the arm outwardly, bend the shoulder joint, and move it inwardly. Now, the myoelectric sensor 32 will be described as an example. The myoelectric sensor 32 is attached to a position Y, which is spaced from an outer end X of the clavicle by a distance of three fingers in a longitudinal direction of the arm. The electrodes of the myoelectric sensor 32 are spaced a given distance apart from each other. The pair of electrodes of the myoelectric sensor 32 is attached to the belly of a muscle to be measured so as to be parallel with the muscle fibers.

Before the myoelectric sensor 32 is attached to the skin surface, the skin surface is scrubbed and cleaned by using alcohol to minimize the resistance between the skin and the electrodes of the myoelectric sensor 32. The electrodes are attached using an electrode paste. The electric resistance between the skin and the electrodes of the myoelectric sensor should be 30 kΩ or less when the myoelectric sensor 32 is attached. The electric resistance between the skin and the electrodes of the myoelectric sensor is preferably 5 kΩ or less when the myoelectric sensor 32 is attached to the skin surface.

The myoelectric sensor 30 is likewise attached to the deltoid muscle of the left shoulder.

The steering angle/steering torque meter 14 is attached around the shaft of the steering wheel of the vehicle to measure the steering angle and the steering torque of the steering wheel. Measurement signals are amplified by an amplifier, which is not shown, digitalized, and transmitted to the evaluation device 16.

The driving load information acquisition unit 18 of the evaluation system 16 calculates representative values from the driving load information (e.g., information on myoelectric potentials, steering angle, and steering torque) transmitted from the biological amplifier 36 and the steering angle/steering torque meter 14.

The driving load information acquisition unit 18 comprises a signal processor for calculating representative values of the myoelectric potentials.

The signal processor performs full-wave rectification and smoothing processing. An RMS (root mean square) for a myoelectric potential signal before the full-wave rectification in a given time range is found, and a change between adjacent data of the myoelectric potential signal after the full-wave rectification and smoothing processing using a low-pass filter is extracted to calculate the amount of change in myoelectric potential. Then the RMS in said given time range for the signal of the amount of change is obtained. Such calculation of the RMS is performed for each myoelectric potential of the right and left deltoid muscles.

Further, the signal processor finds a geometric average of the myoelectric potentials of the right and left deltoid muscles after the full-wave rectification and smoothing processing to obtain a waveform from the geometric average as a simultaneous contraction waveform for the right and left deltoid muscles. Further, an RMS for this simultaneous contraction waveform in said given time range is obtained. Further, a change between adjacent data in the simultaneous contraction waveform is extracted to calculate the amount of change in the simultaneous contraction waveform. Then, an RMS in said given time range for the waveform of this amount of change is obtained.

Thus, the signal processor obtains the RMS (value of the stationary component) of the myoelectric potentials of the right and left deltoid muscles, the RMS (value of the nonstationary component) of the amount of change of the myoelectric potentials on the right and left sides, the RMS (value of the stationary component) of the simultaneous contraction waveform of the right and left deltoid muscles, and the RMS (value of the nonstationary component) of the waveform of the amount of change in the simultaneous contraction waveform, all these for the myoelectric potentials of the right and left deltoid muscles.

The signal processor further obtains the RMS (value of the stationary component) in said given time range for the steering angle and the steering torque transmitted from the steering angle and steering torque meter 14. Further, the signal processor extracts the amount of change between adjacent data of the steering angle and the steering torque to calculate the amount of change in the steering angle and the amount of change in the steering torque and obtains the RMS (value of the nonstationary component) in said given time range for the waveform for each amount of change. That is, the signal processor uses the signals from the steering angle and steering torque meter 14 to obtain the RMS for the steering angle and the steering torque and the RMS of the amount of change in the steering angle and the steering torque.

Thus, the ten RMS values obtained by the signal processor are allowed to undergo the principal component analysis to follow as representative values of the driving load information.

Although the present embodiment uses the RMS of the waveforms of the myoelectric potentials of the right and left deltoid muscles before the full-wave rectification as values of the stationary components, the invention allows using the RMS of the smoothed waveforms of the driving load information in said given time range after the full-wave rectification and smoothing processing as values of the stationary components. One may also use standard deviation, dispersion or distribution range of the value of the smoothed waveform of the driving load information after the full-wave rectification and smoothing processing.

The driving load information is measured under various driving conditions to acquire representative values thereof. The driving condition may be varied, for example, by replacing the vehicle or may be varied by replacing the tires attached to the vehicle. Further, the driving condition is considered to vary also where a change is made in driver, running mode, weather condition, road surface condition, time of the day, or traffic situation.

Further, according to the invention, one may use an average of the RMS values acquired each time measurement is repeated a plurality of times under the same driving condition as representative values of the driving load information used for principal component analysis. The acquired representative values of the driving load information are transmitted to the principal component analysis unit 20 and the overall integrated evaluation unit 24.

The principal component analysis unit 20 performs principal component analysis using the transmitted representative values of the driving load information.

The principal component analysis is made using a known analysis method. The representative values of the driving load information are 10 pieces of data as described above, and a group of 10 pieces of data are therefore acquired for each driving condition.

In the principal component analysis, a group of data of representative values for each driving condition is plotted as points in an assumed 10-dimensional space where coordinate axes normal to each other represent the respective items of driving load information in order to determine the directions of straight lines along which the dispersion (scattering) of a group of points is small. First, the direction of a straight line along which the dispersion is the smallest is determined as a principal component 1, a principal component along which the dispersion is the second smallest and which is normal to the principal component 1 is determined as a principal component 2, and a principal component along which the dispersion is the third smallest and which is normal to the principal component 1 and the principal component 2 is determined as a principal component 3. Thus, a group of 10 pieces of data is divided into principal components to examine the characteristics of each principal component.

The principal component analysis unit 20 performs the principal component analysis to find eigenvalues and calculate eigenvectors that determine the directions of a plurality of principal components. The value of each component of the eigenvectors is a weighting coefficient used for the weighted linear sum which is an index of the integrated evaluation as to drivability of a vehicle described later.

Because a weighting coefficient is obtained for each principal component, a plurality of groups of weighting coefficients exist for the respective eigenvalues. From these, principal components that yield a weighted linear sum appropriate for sensory evaluation are selected by referring to the result of driver's sensory evaluation.

The weighting coefficients thus selected are transmitted to the integrated evaluation unit 24. The result of the driver's sensory evaluation referred to for selecting weighting coefficients is data entered through the entry operation unit 22 comprising a keyboard and a mouse.

The integrated evaluation unit 24 uses selected weighting coefficients and representative values of the driving load information transmitted from the driving load information acquisition unit 18 to calculate a weighted linear sum (principal component score) and uses this weighted linear sum to perform overall integrated evaluation of drivability under each driving condition.

An overall integrated evaluation obtained is supplied to the output device 26 and displayed on screen.

Now, the evaluation method by the evaluation device 16 will be described more specifically below.

Figure 3:
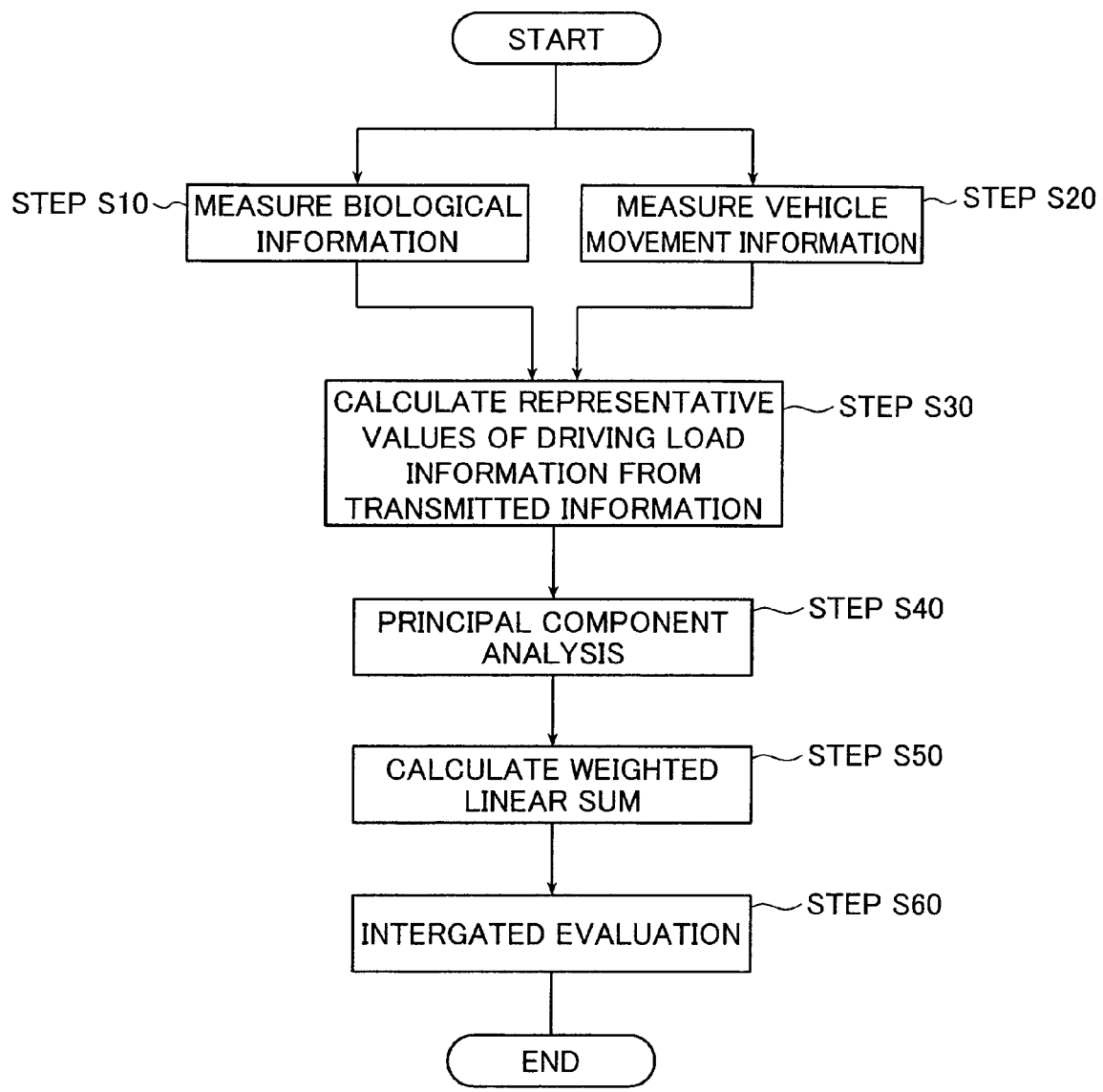
FIG. 3 is a flow chart for explaining the method of evaluating driving conditions of a vehicle according to the invention.

FIG. 3 is a flow chart showing a sequence followed in the method of evaluating driving conditions of a vehicle according to the invention. In the following, a case is described where the myoelectric potentials of the right and left deltoid muscles of the driver are used as biological information whereas the steering angle and the steering torque about the shaft of the steering wheel are used as movement information on the vehicle.

Besides the myoelectric potentials of the deltoid muscles, the biological information may be the myoelectric potentials of the driver's right and left hand side muscles used for voluntary movements to drive the vehicle. Further, the biological information may be information selected from brain waves, respiration rate, body temperature, nictitation frequency, cardiac rate, pulse rate, blood flow rate, amount of perspiration, and electrodermal activity besides myoelectric potentials.

The vehicle movement information preferably includes, besides the steering angle and the steering torque, at least one of a steering angular velocity imparted by the driver to the steering wheel, a steering power imparted by the driver to the steering wheel, a forward/backward acceleration at the vehicle barycenter, a forward/backward jerk at the vehicle barycenter, a lateral acceleration at the vehicle barycenter, a lateral jerk at the vehicle barycenter, a vertical acceleration at the vehicle barycenter, a vertical jerk at the vehicle barycenter, a yaw angular velocity about the vehicle barycenter, a yaw angular acceleration about the vehicle barycenter, a roll angle about the vehicle barycenter, a roll angular velocity about the vehicle barycenter, a side slip angle at the vehicle barycenter, and a side slip angular velocity at the vehicle barycenter. A jerk is a physical quantity obtained by differentiating an acceleration with respect to time.

First, the measuring device 12 measures the biological information (step S10), and the steering angle/steering torque meter 14 measures the vehicle movement information (step S20).

The biological information and the vehicle movement information are measured in the same measuring time range. The biological information is amplified by the amplifier 36 and transmitted after sampling and digitization to the driving load information acquisition unit 18 of the evaluation device 16. The vehicle movement information is amplified and digitalized by the steering angle/steering torque meter 14 and transmitted to the driving load information acquisition unit 18 of the evaluation device 16.

Measurements are made under a plurality of driving conditions. The driving condition is considered to be varied herein when the vehicle differs, the vehicle has different tires attached, the vehicle is driven on a different track, the driving mode such as a running speed differs, the vehicle is driven on a different track surface condition (dry track surface, wet track surface, snow-covered track, etc.), the vehicle is driven at a different time of the day, or the surrounding traffic situation differs.

Next, the driving load information acquisition unit 18 calculates the representative values of the biological information and the vehicle movement information based upon the transmitted information (step S30).

As regards the biological information, the RMS values of the right and left hand side myoelectric potentials in a given measuring time range are calculated to provide representative values. Further, the driving load information acquisition unit 18 performs full-wave rectification and smoothing processing on the myoelectric potential to obtain a smoothed waveform, whereupon differentiation is performed on this waveform to calculate the amount of change between adjacent data, thereby working out the RMS of said amount of change in the given measuring time range. Furthermore, the driving load information acquisition unit 18 performs geometric averaging processing on values for an identical time in the smoothed waveforms of the myoelectric potentials of the right and left deltoid muscles to calculate an RMS for a geometric average thus obtained in the given measuring time range. Further, the amount of change between adjacent data is found by differentiation of the waveform obtained by the above geometric averaging processing to find the RMS of said amount of change in the given measuring time range. The waveform obtained by the geometric averaging processing is used as simultaneous contraction waveform as described in JP 2004-049622 A.

The waveform selected as having the smaller value out of the smoothed waveforms of the right and left myoelectric potentials obtained after smoothing processing in lieu of the geometric averaging processing may be used as simultaneous contraction waveform.

In general, a driver steers the vehicle by operating the steering wheel of the vehicle. To steer the vehicle rightwards, for example, the deltoid muscle of the driver's left shoulder contracts to rotate his/her left hand holding the steering wheel upwards. Meanwhile, the deltoid muscle of the driver's right shoulder relaxes since the driver's right hand need only be placed on the steering wheel. To steer the vehicle leftwards, on the other hand, the deltoid muscle of the driver's left shoulder relaxes whereas the deltoid muscle of the driver's right shoulder contracts. The driver's steering operation performed as described above by contracting one of a pair of deltoid muscles located symmetrically on the right and left sides of the human body and relaxing the other of the pair corresponds, in the present invention, to the antagonistic operation performed by a pair of muscles located symmetrically on the right and left sides of the human body.

However, where a mental load on the part of the driver or difficulty in steering should cause an unnecessary force to be applied to his/her hands holding the steering wheel, a pair of the right and left deltoid muscles contracts in synchronism in the supposedly antagonistic steering operation performed by a pair of the right and left deltoid muscles. A given waveform for the myoelectric potentials obtained from the waveforms of the myoelectric potentials measured at this time is called a synchronous contraction waveform. In this embodiment, such a synchronous contraction waveform is called simultaneous contraction waveform and, as described above, a waveform obtained by geometric averaging processing performed on the waveforms of the myoelectric potentials of a pair of the right and left deltoid muscles is used as simultaneous contraction waveform.

Such contraction of the deltoid muscles produces a force with which the driver holds the steering wheel. However, the force with which the driver holds the steering wheel is information that cannot be acquired as physical measurement data representing a behavior of the vehicle equipped with measuring sensors such as acceleration meters and load cells.

Thus, six RMS values in all are calculated in the step S30: the RMS of the right and left myoelectric potentials, the RMS of the amount of change of the right and left myoelectric potentials, the RMS of the simultaneous contraction waveform of the right and left deltoid muscles, the RMS of the amount of change of the simultaneous contraction waveform.

Figure 4A:
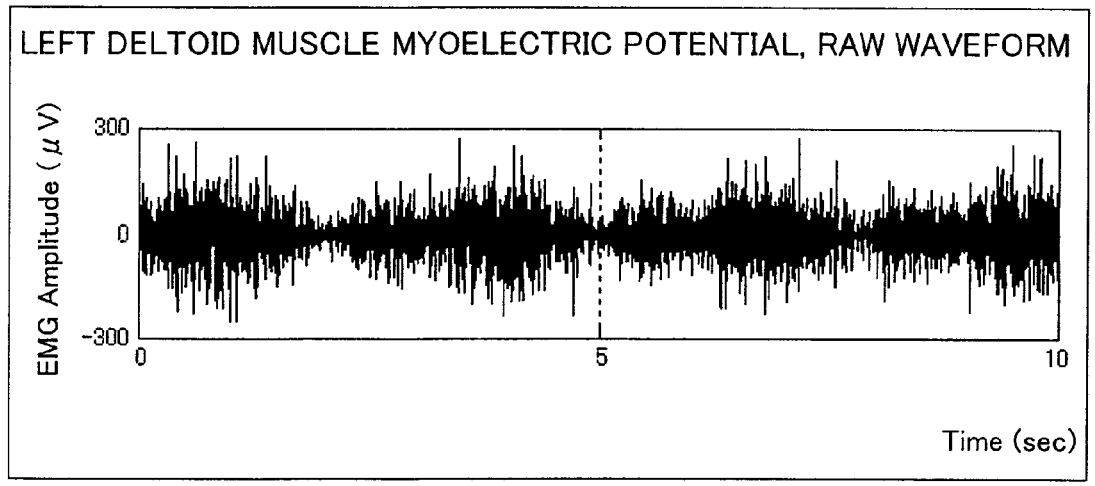
FIGS. 4A to 4F are graphs illustrating examples of data of driving load information acquired in the method for evaluating driving conditions of a vehicle according to the invention.
Figure 4B:
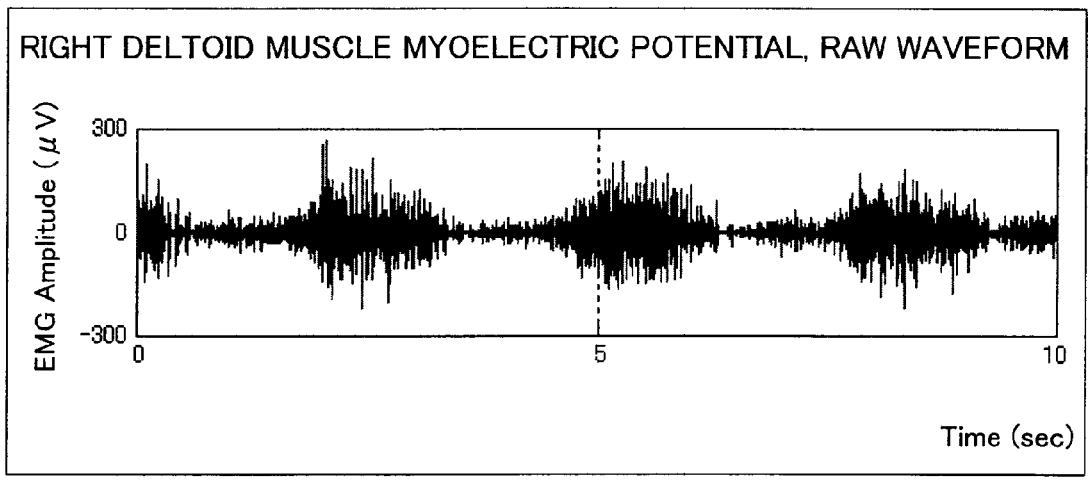
Figure 4C:
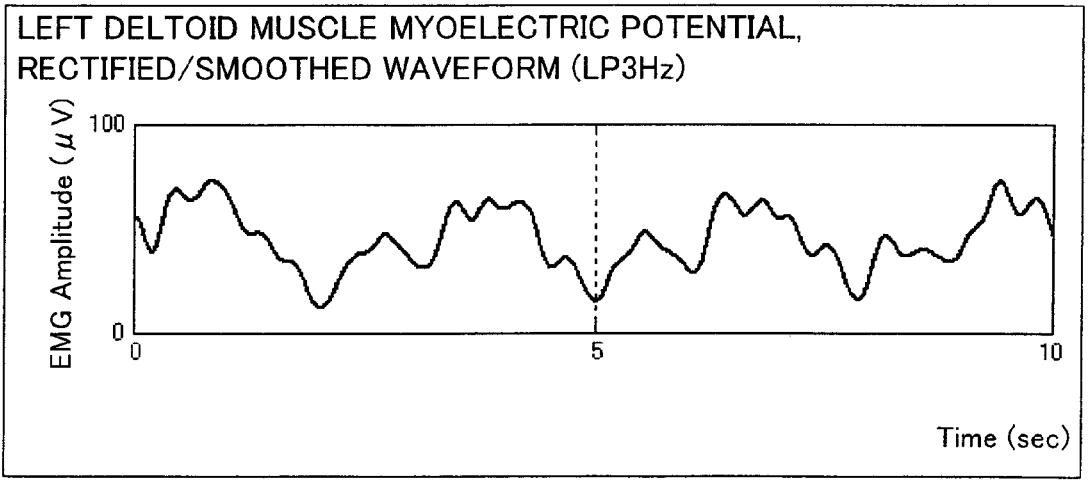
Figure 4D:
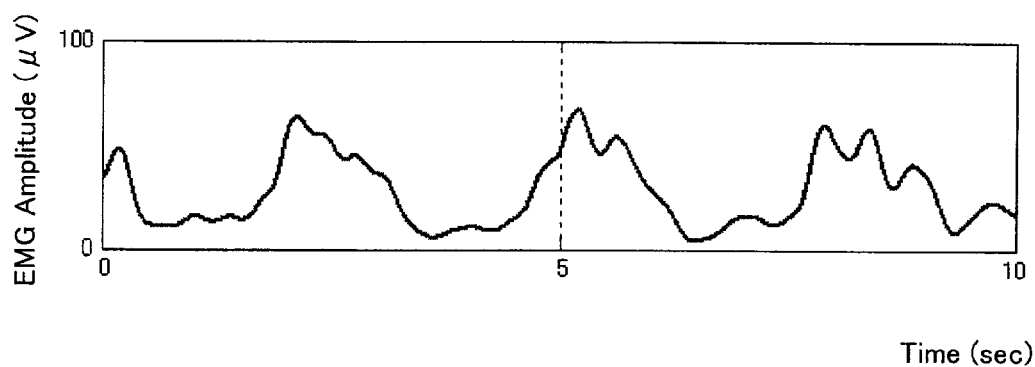

By way of example, FIG. 4A illustrates a waveform of the myoelectric potential of the left deltoid muscle before the full-wave rectification; FIG. 4B illustrates a waveform of the myoelectric potential of the right deltoid muscle before the full-wave rectification. FIG. 4C illustrates a smoothed waveform of the myoelectric potential of the left deltoid muscle after the full-wave rectification and smoothing processing;

FIG. 4D illustrates a smoothed waveform of the myoelectric potential of the right deltoid muscle after the full-wave rectification and smoothing processing.

Further in the step S30, representative values are calculated according to the steering angle and the steering torque. Also in this case, the RMS for the steering angle in the given measuring time range is calculated, and the RMS for the steering torque in the given measuring time range is calculated.

Further, the amount of change between adjacent data is found by differentiation of the time waveform of each of the steering angle and the steering torque to find the RMS of each of the above amount of change in the given measuring time range.

That is, the RMS for the steering angle, the RMS for the steering torque, the RMS for the amount of change in steering angle, and the RMS for the amount of change in steering torque, i.e., four RMS values in total, are calculated as representative values for the information on the steering angle and the steering torque.

Figure 4E:
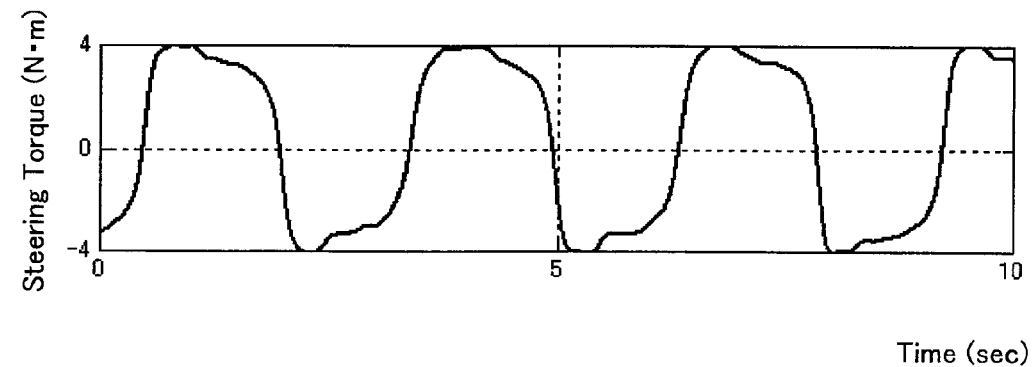
Figure 4F:
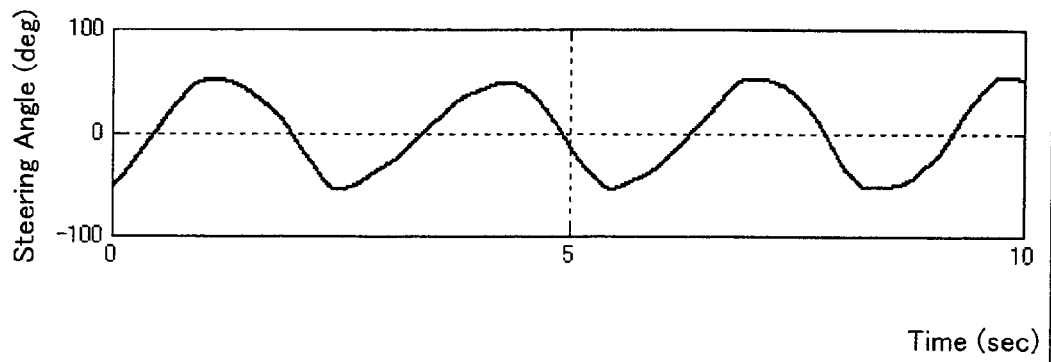

FIG. 4E illustrates an example of waveform of the steering torque; FIG. 4F illustrates an example of waveform of the steering angle. In FIGS. 4E and 4F, the steering torque and the steering angle resulting from turning the steering wheel rightwards are shown as positive values.

The six representative values of the biological information and the four representative values of the vehicle movement information constitute a group of representative values of driving load information under one driving condition. The driving load information acquisition unit 18 acquires groups of representative values of the driving load information respectively for a plurality of driving conditions and transmits these groups to the principal component analysis unit 20.

Next, the principal component analysis unit 20 acquires groups of representative values of the driving load information respectively for a plurality of driving conditions to perform principal component analysis (step S40).

The principal component analysis is made by a known method. In the present embodiment, weighting coefficients used for each weighted linear sum are calculated in such a manner that the scattering or dispersion of the weighted linear sum caused by differences in driving condition is minimal when the weighted linear sum composed of 10 representative values is obtained for 10 representative values for each driving condition. One of weighted linear sums thus obtained can be expressed as evaluation result corresponding to the sensory evaluation obtained from the driver and the like.

Specifically, a variance-covariance matrix for a group of representative values for each driving condition is calculated to find eigenvalues and eigenvectors in the variance-covariance matrix. The eigenvalues are arranged in descending order and accumulated in descending order until a group of eigenvalues is reached where the cumulative eigenvalue exceeds 80% of the sum of all the eigenvalues. The values of the vector components of the eigenvectors for these eigenvalues are the weighting coefficients used for a weighted linear sum of each principal component.

A variance-covariance matrix herein is a matrix of which the nm components are expressed as a covariance (variance when n=m) of a representative value designated for the nth place and a representative value designated for the mth place for a plurality of driving conditions.

FIG. 5 shows examples of 10 representative values obtained in a case where drivers P1 to P8 drove a vehicle equipped with three kinds of tires A, B, and C on the same track at the same running speed and in the same driving mode. Each of the representative values is an average of measurements obtained by repeatedly driving the vehicle under the same driving condition six times. Each of the representative values is a value normalized in such a manner that the average of the representative values with respect to each driver is 1. For example, the average of the RMS values for the steering angle in the case of the driver P1 using the tires A, B, and C is 1.

A normalized representative value herein may be one obtained by dividing each representative value by an average of the representative values for the drivers P1 to P8. Alternatively, one may use a value obtained by subtracting the above average from each representative value. Alternatively, one may use a value obtained by dividing a value obtained by subtracting the above average from each representative value by a standard deviation of the representative values for the drivers P1 to P8. Further, one may use a representative value for a reference tire in lieu of the above average. Such normalization of the representative values allows evening out the magnitudes of the representative values that vary among drivers and eliminates the effects caused by individual differences among drivers.

FIG. 6A shows the result of principal component analysis made for 24 driving conditions involving 8 drivers and 3 kinds of tires. The eigenvalues are 4.92, 2.96, and 0.86 as arranged in descending order. Here, eigenvalues whose cumulative contribution ratio to the sum total of the eigenvalues (=cumulative eigenvalue/total sum of the eigenvalues) is less than 0.8 are 4.92 and 2.96. That is, eigenvalues contributing to this cumulative contribution ratio are taken out on the condition that the cumulative contribution ratio is less than 0.8. Accordingly, the eigenvalue 4.92 and its eigenvector are matched as principal component 1; the eigenvalue 2.96 and its eigenvector are matched as principal component 2.

Next, a weighted linear sum is calculated from the ten representative values using the eigenvectors corresponding to the eigenvalues of the principal component 1 and the principal component 2 as weighting coefficients (step S50).

The eigenvectors are obtained using the above variance-covariance matrix and the eigenvalue of the principal component 1 and the eigenvalue of the principal component 2. That is, a group of weighting coefficients as many as or fewer than the number of pieces of the driving load information is obtained.

FIG. 6B shows amounts of principal component loads in the representative values given in FIG. 5. An amount of principal component load represents a correlation coefficient between the value of the weighted linear sum calculated using the weighting coefficients and the representative values obtained from the eigenvectors in each principal component (value of the principal component score) on the one hand and the respective representative values on the other hand. There are six pieces of driving load information having an amount of principal component load for the principal component 1 greater than 0.7 and two pieces of driving load information having an amount of principal component load for the principal component 2 greater than 0.7. Thus, it appears therefrom that the principal component 1 has a closer correlation with the data shown in FIG. 5 than the principal component 2.

Meanwhile, the results of sensory evaluations conducted by the eight drivers as they drove a vehicle under each driving condition is entered through the entry operation unit 22, whereupon the principal component analysis unit 20 finds a correlation coefficient between the sensory evaluation result and the weighted linear sum obtained in the step S50. One of the principal component 1 and the principal component 2 having the greater absolute value of the correlation coefficient is determined as evaluation index that agrees with the sensory evaluation. That is, an evaluation index of drivability is selected by referring to the drivers' sensory evaluation.

Next, the overall integrated evaluation unit 24 finds a weighted linear sum in a selected principal component 1 to perform evaluation for each driving condition (step S60).

Figure 7A:
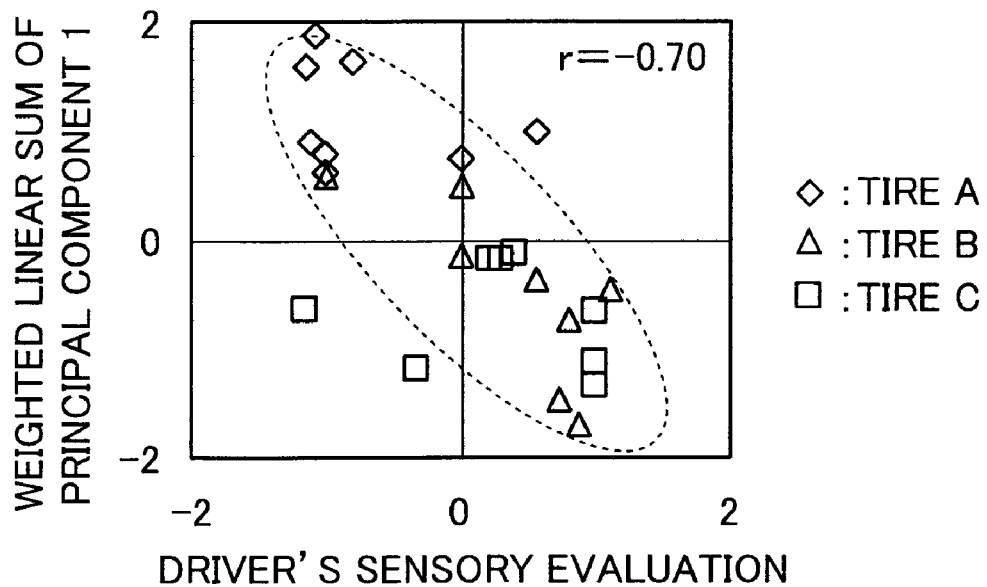
FIGS. 7A and 7B are graphs showing other examples of principal component analysis results obtained in the method for evaluating driving conditions of a vehicle according to the invention.

FIG. 7A is a graph illustrating a correlation between the driver's sensory evaluation result and the weighted linear sum of the principal component 1. As is apparent from FIG. 7A, the weighted linear sum in the principal component 1 has a high negative correlation (correlation coefficient=−0.70) with the sensory evaluation result. Accordingly, the lower the weighted linear sum in the principal component 1 is, the higher, it may be judged, the sensory evaluation is. Thus, the driving conditions can be evaluated using the weighted linear sum in the principal component 1 without relying upon the sensory evaluation.

Figure 7B:
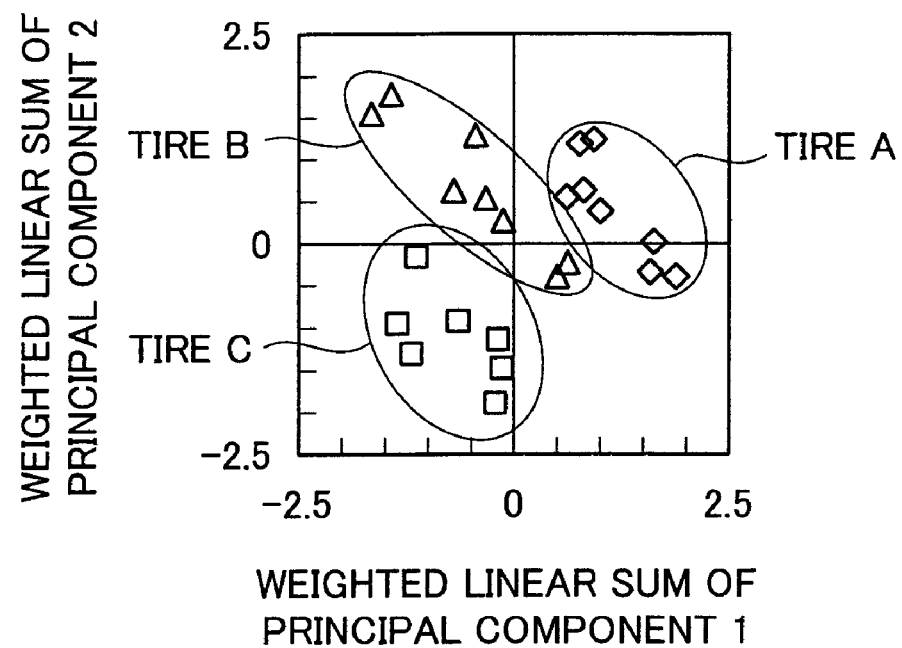

FIG. 7B is a graph illustrating a correlation between the weighted linear sum of the principal component 1 and the weighted linear sum of the principal component 2. It appears from the graph that the tires A, B, and C each form separate groups. Thus, the weighted linear sum of the principal component 2 may be said to be a different evaluation index from the weighted linear sum of the principal component 1.

Since the principal component 2 has a high amount of principal component load in the steering torque and the steering angle among the amounts of principal component loads shown in FIG. 6B, the principal component 2 may be said to be an evaluation index that evaluates the driver's steering load that vary with the magnitude of the steering force applied.

Figure 8A:
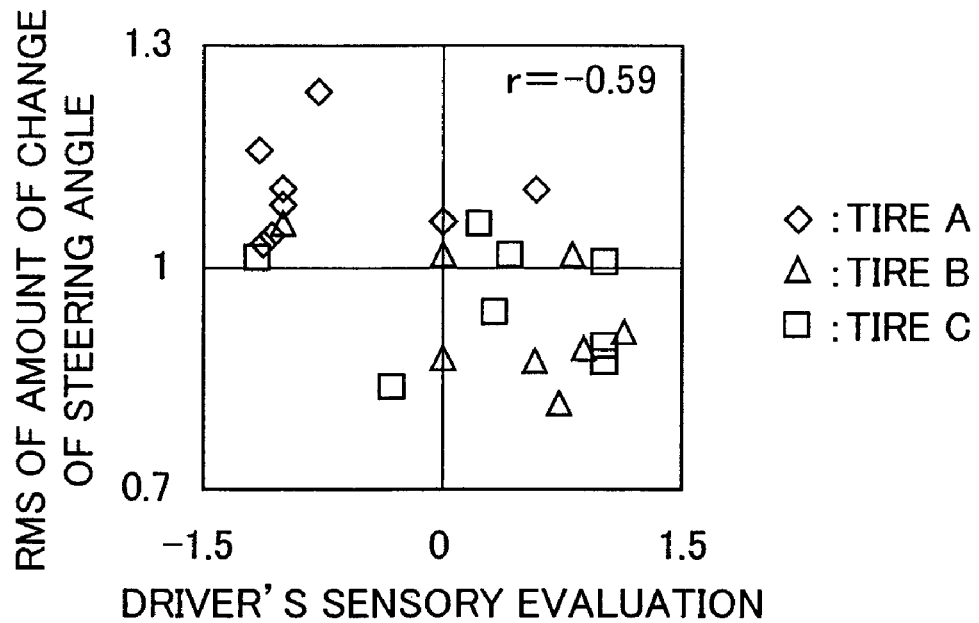
FIGS. 8A and 8B are graphs illustrating relationships between evaluation results and a driver's sensory evaluation results obtained in conventional evaluation methods.
Figure 8B:
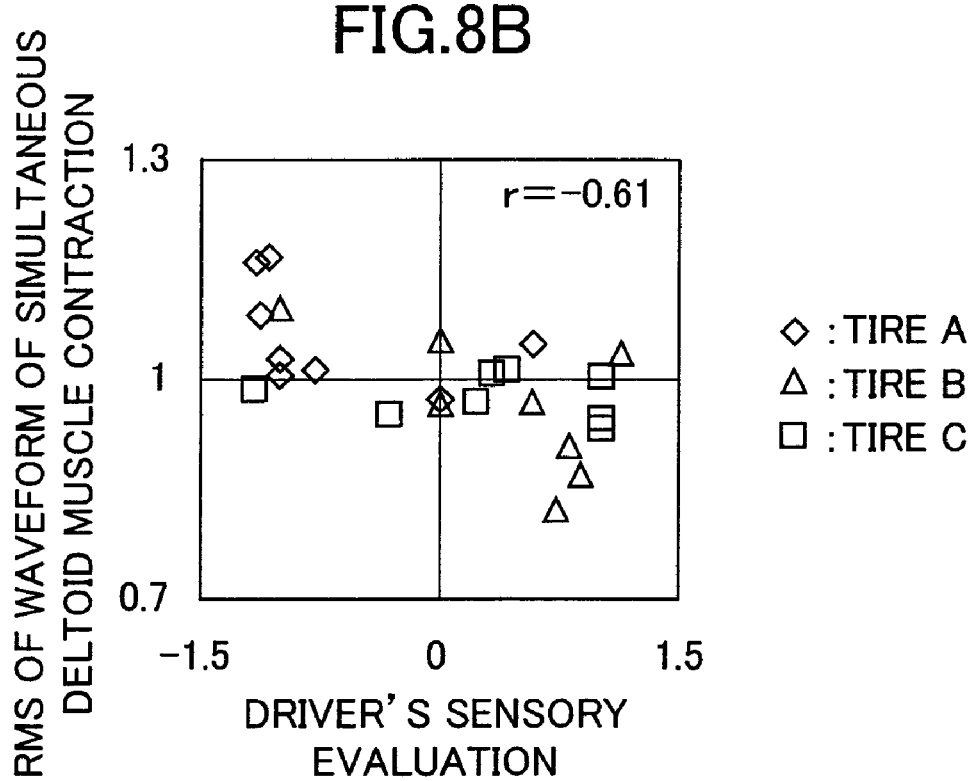

FIG. 8A is a graph illustrating a correlation between the driver's sensory evaluation and the RMS (dRMS.STA) of the amount of change in the steering angle (correlation coefficient=−0.59) used conventionally for evaluation. FIG. 8B is a graph illustrating a correlation between the driver's sensory evaluation and the RMS (RMS.DltLR) of the simultaneous contraction waveform of the driver's deltoid muscles (correlation coefficient=−0.61) used conventionally for evaluation.

It appears therefrom that the correlation shown in FIG. 7A exhibits higher absolute values of correlation coefficients than the correlations shown in FIGS. 8A and 8B, and the evaluation using the principal component 1 corresponds to the driver's sensory evaluation (the smaller the value of the evaluation using the principal component 1 is, the higher the driver's sensory evaluation is).

Figure 9A:
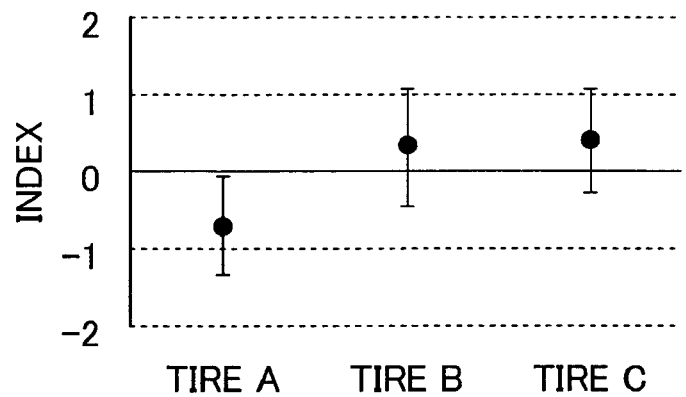
FIG. 9A illustrates an example of result of distribution analysis of driver's sensory evaluation.
Figure 9B:
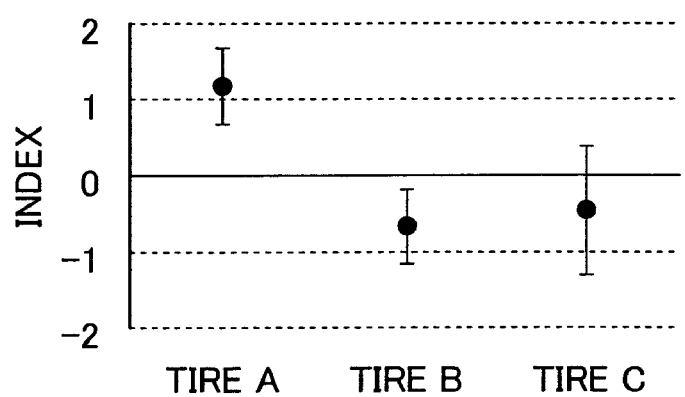
FIGS. 9B and 9C illustrate examples of results of distribution analyses of principal components obtained in the method for evaluating driving conditions of a vehicle according to the invention.

FIG. 9A illustrates averages and standard deviations obtained by variance analysis of the sensory evaluations conducted by the drivers P1 to P8. The tire A and the tire B partially share a common range of standard deviation in such a manner that a judgment as to whether the tire A and the tire B significantly differ is difficult to make. FIG. 9B illustrates averages and standard deviations obtained by variance analysis of the weighted linear sum in the principal component 1. The tire A and the tire B do not share a common range of standard deviation and it is apparent that the tire A and the tire B differ significantly.

Figure 9C:
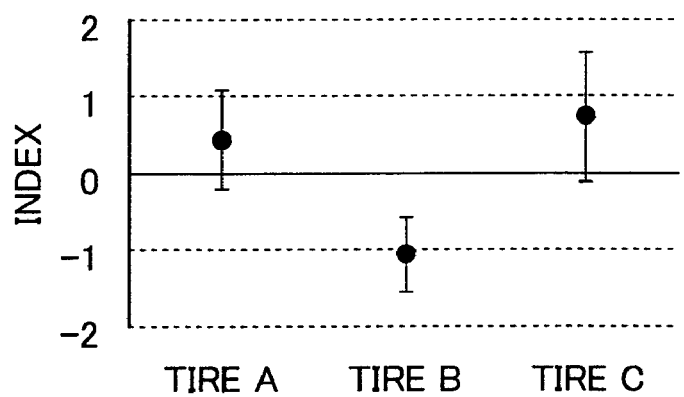

FIG. 9C illustrates averages and standard deviations obtained by variance analysis of the weighted linear sum in the principal component 2. The tire A and the tire B do not share a common range of standard deviation and it is apparent that the tire A and the tire B differ significantly.

Thus, according to the invention, a plurality of pieces of driving load information including biological information on a driving driver and movement information of a vehicle being driven are measured to acquire the respective representative values, and principal component analysis is made using these representative values to calculate a weighted linear sum whereby an accurate overall integrated evaluation of drivability is achieved under each driving condition in a way reflecting the driver's sensations. Further, the overall evaluation of drivability achieved using a weighted linear sum reduces to a minimum the effects of variations attributable to the driver's sensory evaluation. Further, narrowing down from ten representative values to two principal components achieved using such values as a correlation coefficient and a cumulative contribution ratio of an eigenvalue as in the above embodiment enables an objective integrated evaluation of drivability under various driving conditions.

Further, suitability of a tire to a particular vehicle can be evaluated under a driving condition where the same vehicle is driven on the same track, with the tires replaced with different ones. Alternatively, vehicles can be evaluated and their suitability to a particular tire can be evaluated by replacing vehicles, with the other factors unchanged.

Although the above embodiments use the principal component analysis, a factor analysis may be used in lieu of the principal component analysis.

Although the method and the system for evaluating driving conditions of a vehicle according to the present invention have been described above in detail, the present invention is not limited to the above-mentioned embodiments, and various modifications and alterations may be made without departing from the spirit of the present invention.

What is claimed is:

1. A method of evaluating driving conditions of a vehicle whereby drivability of the vehicle driven by a driver under different driving conditions is evaluated, comprising:
   a step of measuring both biological information on a driving driver and movement information of the vehicle being driven as driving load information using one or more sensors, and acquiring a group of representative values, which is obtained from a measurement result of such driving load information, for each driving condition,
   a step of selecting a group of weighting coefficients in a number equal to or less than a number of the representative values of the driving load information from groups of weighting coefficients that are set according to representative values of the driving load information for each driving condition, and
   a step of obtaining a weighted linear sum using a selected group of the weighting coefficients and the group of representative values, and using the weighted linear sum to perform an integrated evaluation of the drivability under each driving condition.

2. The method of evaluating driving conditions according to claim 1, wherein said different driving conditions comprises driving conditions in which the vehicle and a track used for driving are identical and tires attached to the vehicle are varied.

3. The method of evaluating driving conditions according to claim 1, wherein said biological information is information on muscle activities measured as the driver makes voluntary movements to drive the vehicle.

4. The method of evaluating driving conditions according to claim 3, wherein said biological information contains at least one of a stationary component of a muscle activity in a given time and a nonstationary component of a muscle activity in a given time out of information on muscle activities measured as the driver makes the voluntary movements.

5. The method of evaluating driving conditions according to claim 1, wherein said biological information is at least one information selected from myoelectric potentials, brain waves, respiration rate, body temperature, nictitation frequency, cardiac rate, pulse rate, blood flow rate, amount of perspiration, and electrodermal activity.

6. The method of evaluating driving conditions according to claim 1, wherein said movement information of the vehicle contains at least one of a steering angle imparted by the driver to a steering wheel, a steering angular velocity imparted by the driver to the steering wheel, a steering torque imparted by the driver to the steering wheel, steering power imparted by the driver to the steering wheel, a forward/backward acceleration at a vehicle barycenter, a forward/backward jerk at the vehicle barycenter, lateral acceleration at the vehicle barycenter, a lateral jerk at the vehicle barycenter, a vertical acceleration at the vehicle barycenter, a vertical jerk at the vehicle barycenter, a yaw angular velocity about the vehicle barycenter, a yaw angular acceleration about the vehicle barycenter, a roll angle about the vehicle barycenter, a roll angular velocity about the vehicle barycenter, a side slip angle at the vehicle barycenter, and a side slip angular velocity at the vehicle barycenter.

7. The method of evaluating driving conditions according to claim 1, wherein said driving load information is measured for a plurality of drivers, and the representative values of the driving load information are values obtained by normalizing data of the driving load information for each of the drivers.

8. The method of evaluating driving conditions according to claim 1, wherein each of said weighting coefficients is a value of each component of eigenvectors obtained by performing major component analysis on the representative values of the driving load information.

9. The method of evaluating driving conditions according to claim 8, wherein in said step of selecting the group of weighting coefficients, when a cumulative contribution ratio is determined by adding contribution ratios of eigenvalues obtained by the principal component analysis to the sum of all the eigenvalues in descending order, eigenvalues contributing to the cumulative contribution ratio are taken out on the condition that the cumulative contribution ratio is less than 0.8, and values of components of eigenvectors corresponding to the eigenvalues are used as values of the weighting coefficients.

10. The method of evaluating driving conditions according to claim 1, wherein in said step of selecting the group of weighting coefficients, said group of weighting coefficients is selected by referring to a result of a sensory evaluation by the driver.

11. A system of evaluating driving conditions of a vehicle whereby drivability of the vehicle driven by a driver under different driving conditions is evaluated, comprising:
   a unit for measuring a plurality of pieces of driving load information containing biological information on a driving driver and movement information of the vehicle being driven, and acquiring representative values of driving load information obtained from a measurement result of such driving load information,
   a unit for selecting a group of weighting coefficients in a number equal to or less than a number of the representative values of the driving load information from groups of weighting coefficients that are set according to representative values of the driving load information in order to use a weighted linear sum of the representative values of the driving load information as an index of an integrated evaluation of the drivability of the vehicle, and
   a unit for obtaining the weighted linear sum using a selected group of the weighting coefficients and the group of representative values, and using the weighted linear sum to perform the integrated evaluation of the drivability under each driving condition.

* * * * *